United States Patent [19]

Strube et al.

[11] 4,431,807
[45] Feb. 14, 1984

[54] 4-METHYL-5-(UNSUBSTITUTED AND SUBSTITUTED PHENOXY)-6-METHOXY-8-(AMINOALKYLAMINO)QUINOLINES

[75] Inventors: Richard E. Strube, Alexandria, Va.; Maurice P. LaMontagne, Detroit, Mich.

[73] Assignee: The United States of America as represented by the Secretary of the Army, Washington, D.C.

[21] Appl. No.: 328,638

[22] Filed: Dec. 8, 1981

Related U.S. Application Data

[63] Continuation of Ser. No. 158,798, Jun. 12, 1980, abandoned.

[51] Int. Cl.³ .................. C07D 215/20; A61K 31/47
[52] U.S. Cl. ..................................... 546/171; 424/258
[58] Field of Search ........................................ 546/171

[56] References Cited

U.S. PATENT DOCUMENTS 4,209,519  6/1980  Kinnaman ........................ 546/171

OTHER PUBLICATIONS

Chen et al., J. Med. Chem 20, pp. 1107–1109, (1971).
La Mantagne et al., J. Med. Chem, 20, pp. 1122–1127, (1977).

*Primary Examiner*—Paul M. Coughlan, Jr.
*Assistant Examiner*—D. R. Springer
*Attorney, Agent, or Firm*—Ian C. McLeod

[57] ABSTRACT

Compounds of the class including 4-methyl-5-(unsubstituted and substituted phenoxy)-6-methoxy-8-(aminoalkylamino)quinolines as the free bases and pharmaceutically acceptable acid amine salts are described. The compounds are highly effective antimalarial agents which possess, surprisingly, both tissue schizonticidal (radical curative) and blood schizonticidal (suppressive) activity. In addition, these drugs have significantly better therapeutics indices than primaquine which is the current tissue schizonticidal drug of choice. Primaquine possesses no useful blood schizonticidal activity at tolerated dose levels.

14 Claims, No Drawings

4-METHYL-5-(UNSUBSTITUTED AND SUBSTITUTED PHENOXY)-6-METHOXY-8-(AMINOALKYLAMINO)QUINOLINES

This application is a continuation, of application Ser. No. 158,798, filed June 12, 1980, abandoned.

DESCRIPTION OF THE INVENTION

1. Field of the Invention

The present invention relates to compounds of the class including 4-methyl-5-(unsubstituted and substituted phenoxy)-6-methoxy-8-(aminoalkylamino)quinolines which are useful as antimalarials in mammals. A substituted phenoxy group which is trifluoromethylphenoxy is preferred.

2. Prior Art

The class of compounds with which the present invention is concerned generally includes primaquine, 8-((4-amino-1-methylbutyl)amino)-6-methoxy-quinoline, which has the formula:

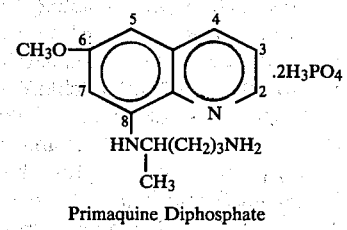

Primaquine Diphosphate

Primaquine, over the years, has been the clinical drug of choice with widespread use in the treatment of refractory, relapsing Plasmodium vivax, P. malariae and P. ovale malaria. Primaquine, used clinically as the diphosphate salt, is a radical curative drug which is effective in clearing the tissues of parasites, but it has only very minimal suppressive activity, i.e., it is relatively ineffective as a blood schizonticide. In man, the toxicity of primaquine precludes administration of a single curative dose. Thus to achieve a radical cure of P. vivax in man, the dose is ordinarily given in divided doses over 14 to 21 days. This is accompanied with a three-day course of chloroquine (a suppressive drug to clear the blood of schizonts) which may "leak" from the tissue cycle of parasite development. No useful drug has been reported which combines both radical curative and suppressive activity, nor has a drug been discovered which is significantly better than primaquine in terms of radical curative activity alone.

As part of early attempts to improve primaquine, the side chain attached to the 8-position of the quinoline nucleus was variously modified as part of the extensive Army World War II Program, but no significant improvement was achieved.

Later in 1955, Elderfield and co-workers, Journal of the American Chemical Society, 77, 4816 (1955), reported the synthesis of 4-methylprimaquine which, more recently, has been tested in modern and well-developed test systems and represents one of two examples in the prior art with radical curative activity comparable to primaquine. The results for 4-methylprimaquine, relative to primaquine, are shown in Table I for both radical curative and suppressive activity

TABLE I

| | Comparison of the Antimalarial Activity of the Better Prior Art Radical Curative Drugs with Primaquine | | | | | | | | |
|---|---|---|---|---|---|---|---|---|---|
| | Suppressive Activity P. Berghei, Rane Mouse Test Dose, mg/kg; ΔMST, Days; 5 mice | | | | | Radical Curative Activity P. cynomolgi, Seato Rhesus Dose, mg/kg (× 7) | | | |
| Compound | 40 | 80 | 160 | 320 | 640 | 3.16 | 1.3 | 1.0 | 0.316 |
| Primaquine Diphosphate | I | I | 9(A) | 2/5T | 5T | | 6/6C | 1/2C | 0/2C |
| 4-Methylprimaquine | I | I | 9(A) | 10(A) | 3C, 1T | | | 2/2C | 0/4C |
| 5-(4-Fluorophenoxy) Primaquine | I | 7.0(A) | 9(A) | 5C | 5C | 1/1C | | 1/3C | 0/2C |

I = Inactive, A = Active, increase in survival time at 7 days or more relatve to controls; T = Toxic Death, C = Cures.

The data indicate that 4-methylprimaquine, as a radical curative drug, is comparable to primaquine and essentially equivalent in efficacy. Thus, 4-methylprimaquine gives 100% cures at 1.0 mg/kg, whereas primaquine gives 100% cures at 1.3 mg/kg and 50% cures at 1.0 mg/kg (½ cures). Both are inactive at 0.316 mg/kg. In the suppressive test, both display very weak activity at non-toxic dose levels, and 4-methylprimaquine is curative only at the toxic dose of 640 mg/kg. Subsequent modifications in the 4-position, M. P. LaMontagne, et al, Journal of Medicinal Chemistry, 20, 1122 (1977), failed to yield a more effective analog.

Concurrently E. M. Chen, et al Journal of Medicinal Chemistry, 20, 1107 (1977) reported the preparation of a series of 5-substituted analogs of primaquine. Of the series of compounds reported in the cited reference, the most active representative was 5-(4-fluorophenoxy)-primaquine, the results for which are shown also in Table I. The compound is no more active than primaquine as a radical curative drug. It is also active and non-toxic as a suppressive drug at the high dose levels of 320 and 640 mg/kg; while this is a slight improvement relative to primaquine, it is distinctly inferior to newly developed clincal suppressive drugs such as mefloquine which is curative in the Rane Test at dose levels as low as 20 mg/kg. Accordingly, 5-(4-fluorophenoxy)primaquine is not an effective suppressive drug and its radical curative activity is not significantly better than that of primaquine.

Thus, in terms of the principles of invention, it is clear that modifications of the 5-substituent, in combination with the 4-methyl substituent, would not be expected by one skilled in the art to yield drugs which would be markedly superior to primaquine as radical curative agents, and which would also be effective suppressive drugs equal or superior to currently-available clinical drugs. It will be demonstrated that this unexpected result has, in fact, been achieved by the new drugs which form the subject matter of this invention.

OBJECTS OF THE INVENTION

It is therefore an object of this invention to provide a novel series of primaquine analog compounds which are unexpectedly active as antimalarial agents at very low dose levels and which are unexpectedly effective against both tissue and blood schizonts. That is, they are both radical curative and suppressive antimalarial agents.

GENERAL DESCRIPTION OF THE INVENTION

The present invention relates to compounds of the formula:

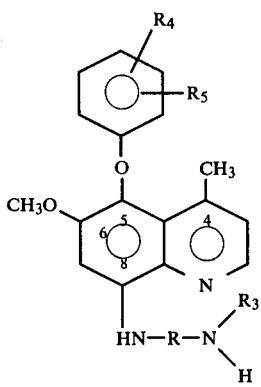

wherein R is an alkylene group which is

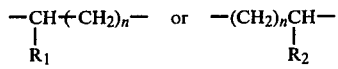

wherein n is 3 or 4, wherein $R_1$ and $R_2$ are methyl or ethyl; wherein $R_3$ is hydrogen or isopropyl, wherein $R_4$ and $R_5$ are hydrogen, chloro, bromo, fluoro, trifluoromethyl or methoxy groups, and wherein the compound is a free amine or a pharmaceutically acceptable acid amine salt.

The pattern of worth for representatives of Structure A have been established through the use of highly standardized tests in experimental animals. The preferred mode for administering these compounds consists in the use of non-toxic acid-addition salts, inclusive of those formed from structure A and acids such as hydrochloric, hydrobromic, succinic, sulfamic, sulfuric, phosphoric, citric, tartaric, methanesulfonic, isethionic, aceturic, malic, fumaric, beta-resorcylic, or pamoic acid. Said salts may be administered orally in the form of tablets, capsules, or dragees when admixed with solid excipients such as lactose, sucrose, starch, microcrystalline cellulose, magnesium stearate or talc. The foregoing compositions are preferred means for oral administration over the use of flavored syrups or tinctures containing the antimalarial drug. Under special circumstances, parenteral administration may be indicated, employing an aqueous solution or an oleaginous formulation of the agent. Aqueous solutions can be prepared in water, physiological saline, Ringer's solution, or the like, either with or without buffers. Oleaginous formulations may be made in natural oils (as, peanut oil or olive oil), or in benzyl benzoate, for example. The several possible isomeric forms of Structure A are to be included among the preferred antimalarials, and advantage may accrue in the choice of one or other of these. The preferred compounds within this class are:

1. 8-((4-Amino-1-methylbutyl)amino)-6-methoxy-4-methyl-5-(3-trifluoromethylphenoxy)quinoline
2. 8-((4-Amino-1-pentyl)amino)-6-methoxy-4-methyl-5-(3-trifluoromethylphenoxy)-quinoline
3. 8-((5-Amino-1-hexyl)amino)-6-methoxy-4-methyl-5-(3-trifluoromethylphenoxy)quinoline
4. 8-((4-Amino-1-ethylbutyl)amino)-6-methoxy-4-methyl-5-(3-trifluoromethylphenoxy)-quinoline
5. 8-((4-Isopropylamino-1-methylbutyl)amino)-6-methoxy-4-methyl-5-(3-trifluoromethylphenoxy)-quinoline
6. 8-((4-Amino-1-methylbutyl)amino)-6-methoxy-5-(4-methoxyphenoxy)-4-methyl-quinoline
7. 8-((4-Amino-1-methylbutyl)amino)-5-(3,4-dichlorophenoxy)-6-methoxy-4-methylquinoline
8. 8-((4-Amino-1-methylbutyl)amino)-5-(2,4-dichlorophenoxy)-6-methoxy-4-methylquinoline
9. 8-((4-Amino-1-methylbutyl)amino)-5-(4-fluorophenoxy)-6-methoxy-4-methylquinoline The compounds as the acid amine salts are more water-soluble than the free amines and are more efficiently utilized in infected animals. The preferred salts include phosphate, citrate and succinate. As salts, the compounds may be hydrated. The present invention relates to the improvement in the process for preparing a 4-methyl-5-(unsubstituted or substituted phenoxy)-6-methoxy-8-nitroquinoline as a product the new and novel steps which comprise: providing 4-methyl-5-fluoro or chloro-6-methoxy-8-nitroquinoline; and displacing the 5-fluoro or 5-chloro group with a phenoxy group in a polar solvent in the presence of an alkali metal hydroxide or an alkali metal carbonate such as potassium carbonate to form the product. Finally the present invention also relates to the improvement in the process for preparing a 4-methyl-5-(unsubstituted or substituted phenoxy)-6-methoxy-8-nitroquinoline as a product the steps which comprise: reacting 4-methyl-5-,6-dimethoxy-8-nitroquinoline with an acid to produce 4-methyl-5-hydroxy-6-methoxy-8-nitroquinoline; displacing the 5-hydroxy group with a chloro group by reaction with phosphorus oxychloride to form 4-methyl-5-chloro-6-methoxy-8-nitroquinoline; and displacing the 5-chloro group with a phenoxy group by reaction with a substituted alkali metal phenoxide in a polar solvent to form the product. The phenyl group can be unsubstituted phenoxy or substituted phenoxy, including particularly mono- or dichloro, monofluoro, trifluoromethyl or methoxy groups in the phenyl ring.

ANTIMALARIAL TESTING PROCEDURES IN ANIMALS

Test Protocols

The two principal testing systems used in this work to evaluate efficacy of candidate drugs are described below.

Radical Curative Test in Rhesus Monkeys, SEATO Medical Research Laboratory, Bangkok, John Brown/Richard Andre This test is designed to evaluate the tissue schizonticidal (radical curative) activity of test compounds. Well-conditioned Indian rhesus monkeys of either sex weighing 2-4 Kg are utilized. Plasmodium cynomolgi (strain B) sporozoites are prepared by grinding heavily infected Anopheles dirus salivary glands in 1:1 monkey serum-saline vehicle.

Method

Monkeys are infected by I.V. injection of $10^6$ freshly isolated P. cynomolgi sporozoites on day 0. A rapidly rising parasitemia develops after a 7-9 day prepatent period, and administration of the test drug is initiated when the rising parasite count exceeds 5000 per mm$^3$ (typically day 10-12). Test drugs are administered orally (by nasogastric intubation) once daily for 7 consecutive days in aqueous solution or, if insoluble, in suspension in 0.3% methylcellulose solution. Chloroquine diphosphate (3.1 mg/kg base/kg orally per day) is always administered concurrently with the test drug for 7 days to eliminate blood schizonts. Thus any tissue schizonticidal activity of the test drug will always be apparent even if it lacks blood schizonticidal activity.

A vehicle control monkey and a positive drug control (primaquine) monkey are included in each group of inoculated monkeys.

Interpretation

The effect of the test drug is determined by counting blood parasites. Parasite counts are made daily through day 20, and every two days thereafter. Initially a clearance of blood parasites is observed due to the blood schizonticidal action of chloroquine. If exoerythrocytic parasites ("tissue schizonts") survive the action of the test drug (i.e. if the drug is inactive or incompletely active) there will be a "relapse" of blood parasites. If there is no relapse within 20 days of the initial clearance of parasitemia, the monkey is splenectomized and its parasitemia followed for an additional 30 days. If there is no relapse within this period, the experiment is terminated and the monkey is considered "cured".

Primaquine diphosphate cures over 90% of monkeys in this test system when administered at a dose of 1.3 mg/kg of salt per day for 7 days (1.0 mg/kg free base) in combination with chloroquine.

References

1. Schmidt, L. N., Rossan, R. N., Fradkin, R., Woods, J. *Studies on the Antimalarial Activity of 1,2-Dimethoxy-4-(bis-diethylaminoethyl)-amino-5-bromobenzene.* Bull. Wld. Health Organ. 34: 783–788, 1966.
2. *WHO report of Procedures for Screening Potential Antimalarial Compounds* held Oct. 26–29, 1971, WHO/MAL/72.763.

Blood Schizonticidal Test (Mouse), University of Miami, Rane (Suppressive)

This system is based on comparisons of responses to test compounds by Plasmodium berghei KBG 173 malaria in mice as expressed in mean survival times and the mean survival times of untreated controls. Thus, compounds noted as active produce increases in the survival times of the treated animals that are significant when compared with the survival times of untreated controls. Since an established disease is less sensitive to treatment than a disease in the early stages of development, treatment is withheld until the parasitemia is relatively high in order to insure a more reliable assay of activity and the selection of appropriate compounds for intensive preclinical studies.

Utilizing young ICR/HA Swiss mice and a standard inoculum of Plasmodium berghei KBG 173, it is possible to produce a uniform disease fatal to 100% of untreated animals within 6 to 8 days with a mean survival time of 6.2 days. Test animals weigh from 18 to 22 grams but weight variations in any given experimental or control group are confined to 2–3 grams. All animals in any given test are approximately of the same age. Animals on test are housed in metal-topped plastic cages, given a standard laboratory diet and water ad libitum.

Test animals receive an intraperitoneal injection of 0.5 ml of 1:100 dilution of heparinized heart's blood with a minimum of 90% parasitized cells ($4 \times 10^7$ cells), drawn from donor mice infected one week earlier with Plasmodium berghei. The donor stran is maintained by weekly passages in separate groups of mice inoculated with a 0.5 ml of 1:500 dilution of heparinized heart's blood.

Test compounds are administered after dissolution or suspension in peanut oil. A single dose is given subcutaneously 72 hours after the mice are infected with Plasmodium berghei. At this time a 10–15 percent parasitemia has developed; the disease is well established but has not produced sufficient debility to alter the response of the host to toxic effects of the drug on test. Since treatment is withheld for three days to permit the infection to become well established and death occurs in untreated controls within 6–8 days, it is believed that this system presents a candidate compound with the maximum challenge. In order to check factors such as changes in the infectivity of Plasmodium berghei or in the susceptibility of the host or to detect technical errors, a group of infected animals treated with pyrimethamine at dose levels producing definite increases in survival time is included as a positive control in every experiment.

In each experiment test compounds are administered in graded doses. With highly active compounds, increases in dose levels are usually followed by increases in the survival time of the treated mice. However, if an active drug is toxic for the host, its toxicity may become a limiting factor; continued increases in dose levels also increase the toxic effects and may result in the diminution of survival times. Deaths prior to the sixth day, when untreated controls begin to die, are regarded as non-parasitic and become the basis for toxicity evaluations. Treated animals are kept under observation for 60 days. Survivors at the end of this period of time are considered as cured.

An increase of 100% in mean survival time is considered the minimum effective response for a candidate compound. In calculating mean survival time, toxic deaths and 60 day survivors are not included.

References

1. Osdene, T. S., Russell, P. B. and Rane, L. *2,4,7-Triamino-6-ortho-substituted Arylpteridines. A New Series of Potent Antimalarial Agents.* J. Med. Chem. 10, 431–434, 1967.

Antimalarial Activity Test Data

The antimalarial activity data acquired by the two test procedures described above are listed in Tables 2 and 3 for the compounds of this invention. In Table 4, the most promising compound of the series, compound 1, is compared directly with primaquine together with some additional test data for compound 1 compared to primaquine. In all the work reported herein primaquine is used in the form of the diphosphate salt. The test data are expressed in the form of the number of cures at a given dose level. Extension of life (mean survival time) relative to the controls is noted in the Rane mouse test;

if the mean survival time is extended seven or more days, the compound is considered to be active.

The Molar Primaquine Index is useful in the radical curative test (Table II) as a gauge of the efficacy of a candidate drug relative to primaquine. In the $CD_{100}$ index, the dose (in moles) at which the new drug achieves 100% cures is divided into the dose (in moles) at which primaquine demonstrates 100% cures.

Table II (Radical Curative Test)

Table II lists the radical curvature activity data for the nine new compounds relative to primaquine.

Table 3 (Suppressive Test)

Referring to Table 3, the same nine compounds are compared to primaquine in the suppressive test (vs. blood shizonts). In this test, compound 5 is totally ineffective and the other eight compounds are markedly superior to primaquine. The results for these eight compounds are very significant. All eight are curative at 20 mg/kg and six are curative at 10 mg/kg. These results are equal or superior to the newer clinical suppressive drugs such as mefloquine which is curative at 20 mg/kg in this test system.

TABLE II

**RADICAL CURATIVE ACTIVITY OF 4-METHYL-5-ARYLOXYPRIMAQUINE ANALOGS
SEATO PRIMATE ANTIMALARIAL STUDY**
*Plasmodium Cynomolgi* - Rhesus Monkey - Sporozoite Induced Test

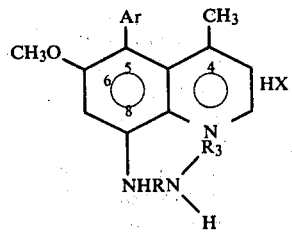

| | Ar = Aryloxy | | | Salt | P. cynomolgi (Rhesus) dose (Mg/kg × 7) of Salt | | | Molar Primaquine Index |
| --- | --- | --- | --- | --- | --- | --- | --- | --- |
| CPD No. | Ar | R | $R_3$ | Form | 1.0 | 0.316 | 0.1 | CD 100 |
| 1 | $-OC_6H_4CF_3(m)$ | $-CH(CH_2)_3-$ <br> $\|$ <br> $CH_3$ | H | S | 2/2C | 2/2C | 0/2C | 4.8 |
| 2 | $-OC_6H_4CF_3(m)$ | $-(CH_2)_3CH-$ <br> $\|$ <br> $CH_3$ | H | S | 2/2C | 2/4C | 0/2C | 1.3 |
| 3 | $-OC_6H_4CF_3(m)$ | $-(CH_2)_4CH-$ <br> $\|$ <br> $CH_3$ | H | S | 2/2C | 0/2C | 0/2C | 1.3 |
| 4 | $-OC_6H_4CF_3(m)$ | $-CH(CH_2)_3-$ <br> $\|$ <br> $CH_2CH_3$ | H | S | 2/2C | 1/2C | 0/2C | 1.3 |
| 5 | $-OC_6H_4CF_3(m)$ | $-CH(CH_2)_3-$ <br> $\|$ <br> $CH_3$ | $-CH(CH_3)_2$ | S | 3/3C | 1/2C | 0/2C | 1.3 |
| 6 | $-OC_6H_4OCH_3(p)$ | $-CH(CH_2)_3-$ <br> $\|$ <br> $CH_3$ | H | MP | 3/3C | 2/2C | 0/2C | 4.6 |
| 7 | $-OC_6H_3Cl_2(m,p)$ | $-CH(CH_2)_3-$ <br> $\|$ <br> $CH_3$ | H | MP | 3/3C | 1/2C | 0/3C | 1.3 |
| 8 | $OC_6H_3Cl_2(o,p)$ | $-CH(CH_2)_3-$ <br> $\|$ <br> $CH_3$ | H | MP | 3/3c | 1/2C | 0/3C | 1.3 |
| 9 | $-OC_6H_4F(p)$ | $-CH_3(CH_2)_3-$ <br> $\|$ <br> $CH_3$ | H | MP | 3/3C | 2/2C | 0/3C | 4.5 |
| | Primaquine Diphosphate | | | | $1/2C^a$ | 0/2C | 0/2C | 1.0 |

C = Cure
S = Succinate
MP = Monophosphate
$^a$6/6C at 1.3 mg/kg

Overall, three compounds 1, 6 and 9 are markedly superior to primaquine as radical curative drugs. In the suppressive test, compounds 1 and 9 are both curative at 10 mg/kg but compound 9 is somewhat more toxic. On this basis compound 1 was rated the most effective and promising drug and was selected for further evaluation. It must be reemphasized that all of the nine compounds are superior to primaquine in the radical curative tests and eight are markedly superior to primaquine in the suppressive tests.

TABLE III

SUPPRESSIVE ANTIMALARIAL ACTIVITY DATA
P. berghei, Rane Mouse Test, Five Mice
(See Table II for Compound Structures)
Dose, mg/kg ($\times$ 1), S. C.

| Compound Number | 5 | 10 | 20 | 40 | 80 | 160 | 320 | 640 |
|---|---|---|---|---|---|---|---|---|
| 1 | 1C | 3C | 5C | 5C | 5C | 5C | 5C | 1C, 4T |
| 2 |  | I | 4C | 5C |  |  |  |  |
| 3 | 13(A) | 3C | 5C | 5C | 4C | 4C |  |  |
| 4 | I | 3C | 5C | 5C | 5C | 5C | 5C | 2C, 3C |
| 5 |  |  |  |  |  | I |  | 4T |
| 6 | I | 7(A) | 1C | 5C | 5C | 5C | 5C | 2C, 3T |
| 7 | 4C | 5C | 5C | 5C | 5C | 5C | 5C | 5C |
| 8 | I | 1C | 5C | 5C | 5C | 5C | 4C, 1T | 3C, 2T |
| 9 | 7(A) | 3C | 4C | 5C | 5C | 5C | 4C, 1T | 3C, 2T |
| Primaquine Diphosphate |  |  |  | I | 9(A) I | 2T 9(A) | 5T 2/5T | 5T 5T |

C = Cure (60 days survival)
I = Inactive
A = Active, 7 Days or more estension of survival relative to controls.
T = Toxic Table IV (Summary and Additional Test Data)

Table IV compares compound 1 with primaquine in suppressive activity (Part A, two test systems), radical curative activity (Part B, two test systems) and acute toxicity (Part C) in three animal species. The data for the tests in B-1 and A-1 were reported also in Tables II and III, respectively.

Referring to Table IV, Part A-1 (Rane mouse test), the data clearly demonstrate the marked superiority of compound 1 which displays curative activity down to 10 mg/kg, whereas primaquine is toxic and non-curative at any dose level.

Equally significant is the suppressive activity comparison (Part A-2) in the Rhesus monkey. This test differs from the SEATO radical curative test primarily in that parasitemia is induced by intravenous inoculation of parasitized blood (rather than sporozoites) and that chloroquine is not co-administered with the test drug. Whereas primaquine does possess suppressive activity in the Rhesus, the drug failed to clear the blood schizonts completely as indicated by its failure to achieve cures. On the other hand, compound 1 is curative at doses down to 1.0 mg/kg/day.

In Part B-1 of Table IV, the superiority of compound 1 over primaquine as a radical curative drug is evident. Compound 1 achieved 2/2 cures at 1.0 mg/kg/day whereas primaquine achieved but ½ cures, and compound 1 was 100% curative at 0.316 mg/kg/day whereas primaquine was inactive at this dose level.

In Part B-2 is shown a comparison between primaquine and compound 1 as radical curative drugs when used in conjunction with chloroquine as a suppressive adjuvant. As discussed earlier under Prior Art, Section 2, the toxicity of primaquine precludes administration of a single curative dose and, in order to achieve a radical cure of P. vivax in man, multiple doses are required coupled with the administration of chloroquine to maintain the blood clear of schizonts. Accordingly, the B-1 test was modified to establish whether a single dose of compound 1 was effective as both a tissue and blood schizonticide, and whether the co-administration of chloroquine was necessary and/or desirable. The results are shown in B-2.

The data of B-2 show that primaquine at a dose level of 3.5 mg/kg ($\times$1) in combination with chloroquine was effective although a relapse was observed in one of the four animals. Compound 1, without chloroquine, was equally active at 3.5 mg/kg (with no relapses, but one suppressive failure). On the other hand, the co-addition of chloroquine demonstrates that the fully curative dose level of compound 1 can be reduced to 0.875 mg/kg compared to 14 mg/kg for primaquine. On this basis the Molar Primaquine Index (as defined earlier) with chloroquine co-administration is 19. These ratios clearly demonstrate the superiority of Compound 1 over primaquine against P. cynomolgi in the Rhesus which is regarded as predictive of the efficacy of the drugs against P. vivax in man.

Comparison of 8-((4-Amino-1-methylbutyl)amino)-6-methoxy-
4-methyl-(5-trifluoromethylphenoxy)quinoline
Succinate
(Compound 1 of Tables II and III)
With Primaquine Diphosphate A. Blood Schizonticidal (Suppressive Studies)

1. Rane Mouse Test, P. berghei

| mg/kg, S.C., Salt | Primaquine Diphosphate | Compound 1 |
|---|---|---|
|  | (No Cures) |  |
| 640 | 5/5T | 2/10C (4T) |
| 320 | 2/5T | 5/5C |
| 160 | 9 Days (A) | 10/10C |
| 80 |  | 5/5C |
| 40 |  | 15/15C |
| 20 |  | 10/10C |
| 10 |  | 2/5C |
| 5 |  | 7 Days (A) |

T = Toxic Death; A = Active; C = Cure

2. SEATO Laboratory, P. cynomolgi, Rhesus Monkey Suppressive Tests

| mg/kg, Oral, Salt, $\times$ 7 days | Primaquine Diphosphate | Compound 1 |
|---|---|---|
|  | (No Cures) |  |
| 31.6 | 2/2S |  |
| 10.0 | 2/2S | 2/2C |
| 3.16 | 2/2S | 2/2C |
| 1.0 | 2/2S | 2/2C |

S = Suppressive; C = Cure

B. Tissue Schizonticidal (Radical Curative) Test

1. SEATO Laboratory, P. cynomolgi, Rhesus Monkey, Radical Curative Test

| mg/kg, Oral Salt, $\times$ 7 Days | Primaquine Diphosphate | Compound 1 |
|---|---|---|
| 1.3 | 6/6C | 2/2C |
| 1.0 | 1/2C | 2/2C |
| 0.316 | 0/2C | 2/2C |

2. Combination Drug Therapy including chloroquine as a Suppressive Adjuvant, P. cynomolgi, Rhesus Monkeys, Radical Curative Studies

| mg/kg, Oral Base ($\times$ 1)[a] | Primaquine plus Chloroquine[b] | Compound 1 | Compound 1 plus Chloroquine |
|---|---|---|---|
| 14 | 2C | 1C, 1SF* |  |
| 7 | 2C, 1SF, 1R | 2C |  |
| 3.5 | 2C, 1SF, 1R | 1C, 1SF |  |
| 1.75 | 2R | 4SF | 2C |
| 0.875 |  | 3SF, 1R | 4C |

-continued

Comparison of 8-((4-Amino-1-methylbutyl)amino)-6-methoxy-
4-methyl-(5-trifluoromethylphenoxy)quinoline
Succinate
(Compound 1 of Tables II and III)
With Primaquine Diphosphate

| 0.4375 | 4R | 4R |

*Doubtful data point; expect 2C in view of 2C at 7 mg/kg.
<sup>a</sup>Primaquine or Compound 1b administered in salt form but calculated as the free base. Chloroquine (phosphate) added as 5 mg/kg of salt (× 7).
C = cure, SF = suppressive failure (blood not cleared), R = relapse (tissues not cleared).

C. Acute Toxicity Data

| | Acute Oral LD$_{50}$ Data, mg/kg | | | |
|---|---|---|---|---|
| | Rats | | Guinea | Mice |
| | Male | Female | Pigs, Male | Male |
| Primaquine | 177 | 224 | 54 | 148 |
| Compound 1 | 259 | 577 | 174 | 236 |
| Ratio: Compound 1/ Primaquine | 1.46 | 2.76 | 3.22 | 1.59 |

Finally, in Part C of Table II, the acute toxicity of compound 1 relative to primaquine in three animal species is shown. Compound 1 displays significantly less acute toxicity, in all of these species, than primaquine by factors ranging from 1.5 to 3.2.

EXPERIMENTAL METHODS OF PREPARATION OF THE COMPOUNDS OF THE PRESENT INVENTION

1. General Description

Two synthesis routes have been developed for the preparation of compounds of the present invention. The first route, shown in Chart No. 1, was more extensively studied and will be described first.

Commercially-available veratrole was dinitrated to form 4,5-dinitroveratrole (I) as described in the literature (See, for example, H. Fellner and G. Fellner, Helv. Chim. Acta, 49, 913 (1966) and L. Weinberger and A. R. Day, J. Org. Chem., 24, 1451 (1959). Treatment of Compound 1 with methanolic ammonia under pressure gave 4,5-dimethoxy-2-nitroaniline (II) following literature procedures (See, for example, M. Tomita et al., Yakugaku Zasshi, 71 850 (1951) and R. C. Elderfield et al., J. Am. Chem. Soc. 77, 4816 (1955)).

Compound II was treated with commercially-available methyl vinyl ketone in the presence of phosphoric acid and arsenic acid to afford the intermediate 5,6-dimethoxy-4-methyl-8-nitroquinoline (III), a new compound, as a pure crystalline material in 30% yield. This successful reaction is novel in that the steric hindrance provided by the 2-methoxy group of 4-amino-5-nitroveratrole and by the methyl group of methyl vinyl ketone would be expected by those skilled in the art to prevent the ring-closure reaction to form III from occurring.

Treatment of compound III with hydrochloric acid in ethanol selectively removed one methyl group to afford the 5-hydroxy derivative IV. This was readily converted with phosphorus oxychloride to the 5-chloro derivative V, a key intermediate. It may be noted that intermediate V is the starting material for compounds 1, 6, 7, 8, and 9 of the present invention in which the substituent group in the 5-position is varied.

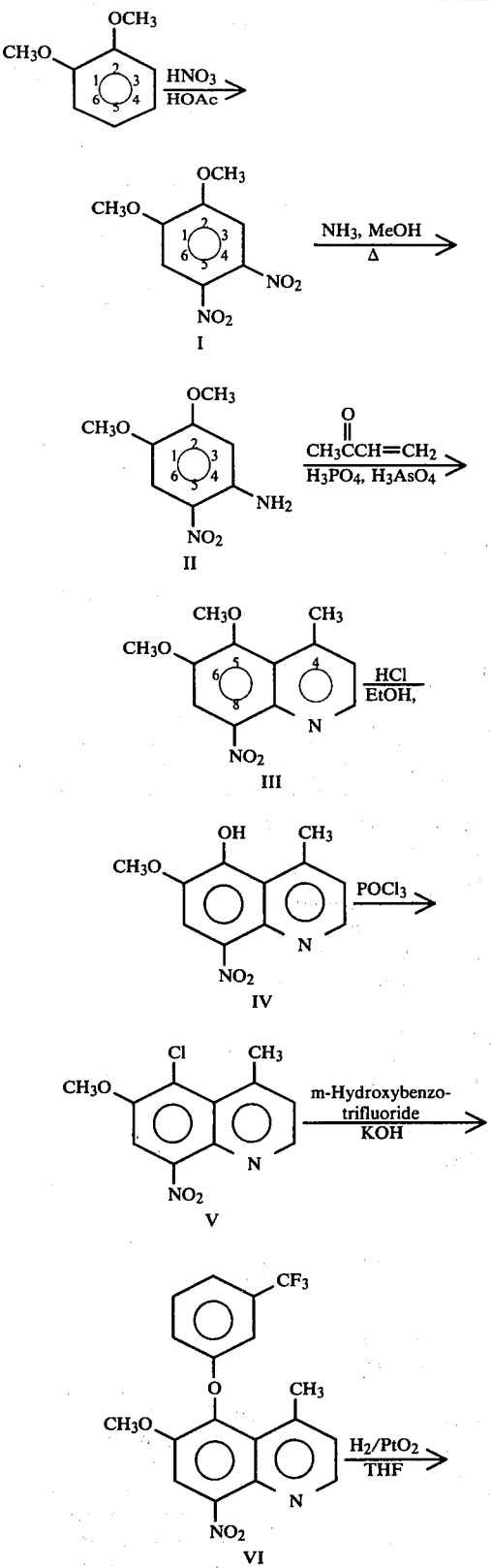

CHART No. 1
8-((4-AMINO-1-METHYLBUTYL)AMINO)-6-METHOXY-4-METHYL-5-(3-TRIFLUOROMETHYLPHENOXY)QUINO-LINE SUCCINATE (1)

-continued
CHART No. 1
8-((4-AMINO-1-METHYLBUTYL)AMINO)-6-METHOXY-4-METHYL-5-(3-TRIFLUOROMETHYLPHENOXY)QUINOLINE SUCCINATE (1)

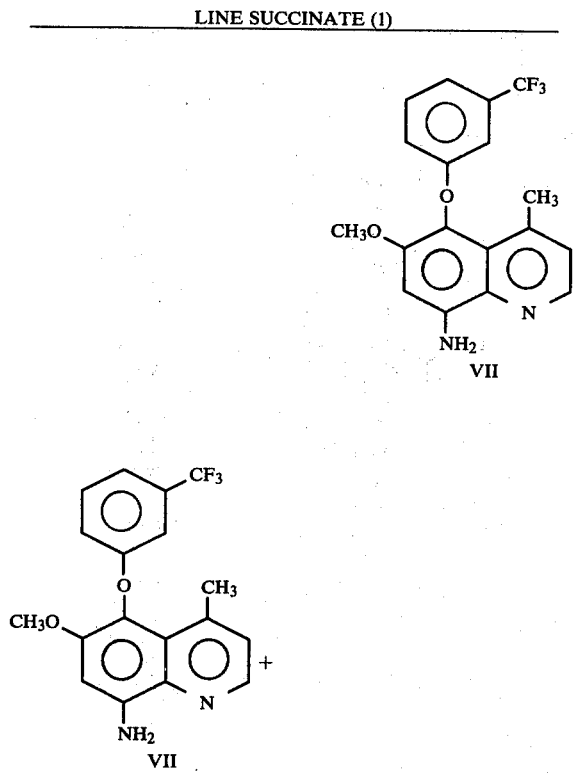

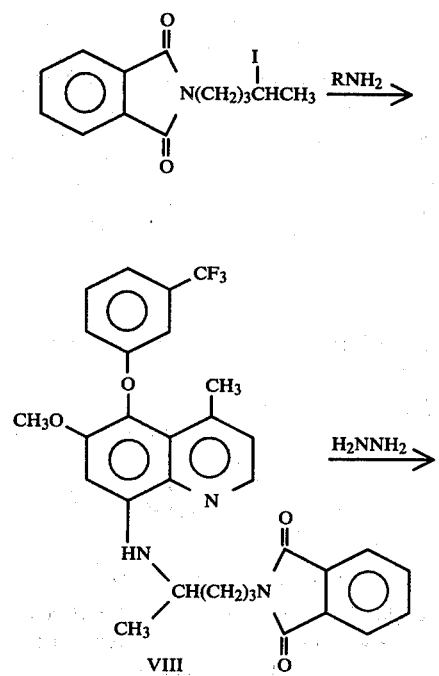

-continued
CHART No. 1
8-((4-AMINO-1-METHYLBUTYL)AMINO)-6-METHOXY-4-METHYL-5-(3-TRIFLUOROMETHYLPHENOXY)QUINOLINE SUCCINATE (1)

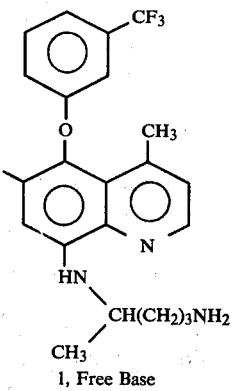

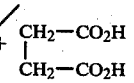

As shown in Chart No. 1, intermediate V was condensed with m-hydroxybenzotrifluoride in a suitable solvent in the presence of potassium hydroxide to form intermediate VI. The 8-nitro group of intermediate VI was reduced by catalytic hydrogenation to the 8-amino derivative VII. It may be noted here that intermediate VII was used not only for the preparation of compound 1 of the present invention, but also for compounds 3, 4 and 5 in which the alkylaminoalkyl group in the 8-position of the molecule was varied.

For the preparation of compound 1, the 8-amino derivative VII was condensed with 4-iodo-1-phthalimidopentane in the presence of a dialkylamine as an acid acceptor to form the protected aminoalkylamine in the 8-position of the molecule as applied by E. M. Chen and co-workers, Journal of Medicinal Chemistry, 20, 1107 (1977) to the 4-desmethyl analog of VII. Alternatively, as described by Chen in the same paper, 4-bromo-1-phthalimidopentane can be employed also in this step.

Compound VIII was deprotected by treatment with hydrazine to form the target compound 1 as the free base. Treatment of the free base with one mole of succinic acid in a suitable solvent system forms the target compound 1 as the succinic acid salt.

In addition to the unexpected success in the ring closure reaction, an important and novel concept of the process shown in Chart No. 1 is the ability to introduce a reactive halogen atom in the 5-position of the molecule and thus provide the key 5-chloro intermediate V.

The procedure used by E. H. Chen et al. J. Med. Chem. 20, 1107 (1977) in which 6-methoxy-8-nitroquinoline was directly halogenated in the 5-position to form the 5-bromo derivative is not applicable to 4-methyl-6-methoxy-8-nitroquinoline. Thus, direct halogenation of the latter compound leads to preferential attack on the 4-methyl group to form the bromomethyl and dibromomethyl derivatives.

An alternative route to compounds of the present invention is shown in Chart No. 2. This route involves the preparation of 4-methyl-5-fluoro-6-methoxy-8-nitroquinoline (XIV) instead of the 5-chloro derivative V (See Chart No. 1). The 5-fluoro group is reactive, as is the 5-chloro group, and can also be treated with substituted phenols in the presence of base to form intermediates such as compound VI of Chart No. 1.

Referring to Chart No. 2, commercially available 2-fluoroanisole was nitrated in acetic anhydride to form 2-fluoro-4-nitroanisole (IX) as described in the literature (See R. C. Elderfield and co-workers, J. Am. Chem. Soc., 68, 1584 (1946)). Reduction of IX with stannous chloride in hydrochloride acid gave 4-amino-2-fluoroanisole (X) as described by G. Schiemann and T. Miau, Ber., Vol 66B, 1179 (1933). The N-acetyl derivative XI was prepared and nitrated to give 4-acetamido-2-fluoro-5-nitroanisole (XII) which was deacylated with base to form the aniline XIII; both steps were described by R. C. Elderfield (loc. cit.). Compound XIII was treated with methyl vinyl ketone in the presence of phosphoric acid and diarsenic pentoxide to form 4-methyl-5-fluoro-6-methoxy-8-nitroquinoline (XIV). In this case, relative to the preparation of compound III (Chart No. 1), steric hindrance is markedly less due to the small size of the fluorine atom. Condensation with m-hydroxybenzotrifluoride in the presence of base gave compound VI, identical to compound VI prepared as shown in Chart No. 1. Thus, as stated, an alternative route to compounds of the present invention is available. Both routes involve the introduction of an active, displaceable (with phenols) halogen atom in the 5-position of the quinoline nucleus by indirect means.

CHART No. 2
ALTERNATE ROUTE TO COMPOUNDS OF
THE PRESENT INVENTION

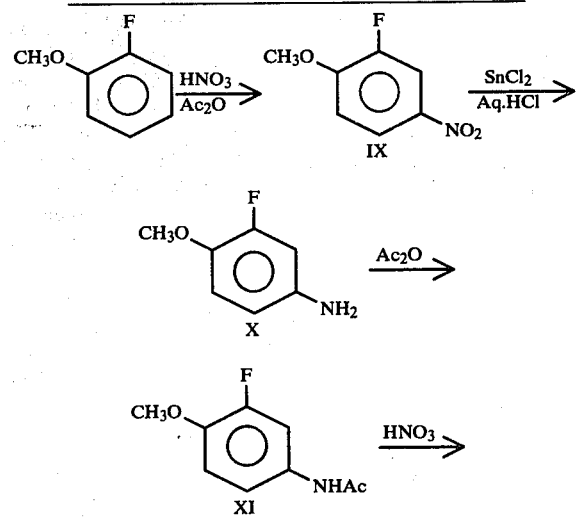

-continued
CHART No. 2
ALTERNATE ROUTE TO COMPOUNDS OF
THE PRESENT INVENTION

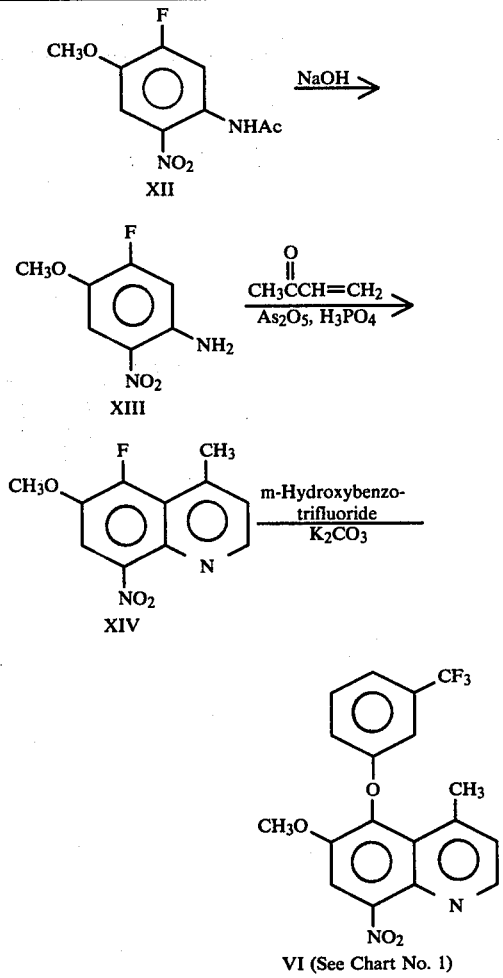

2. Specific Description

The processes for the preparation of the compounds of the present invention are described in the following Examples 1 to 9. All temperatures are in °C. and melting points and boiling points are uncorrected. NMR spectra were determined on a Varian Model T60A spectrometer. Ethanol used in this work was specially denatured Grade 3A alcohol (90% ethanol, 5% isopropanol and 5% methanol by volume).

EXAMPLE 1

8-(4-Amino-1-methyl-butylamino)-6-methoxy-4-methyl-5-(3-trifluoromethylphenoxy)quinoline Succinate The title compound was made by the route shown in Chart No. 1 and includes the preparation of intermediates I through VIII, as well as compound 1, free base, and compound 1, succinic acid salt.

An alternative route to intermediate VI also forms part of Example 1.

4,5-Dinitroveratrole (I)

A 22 L three-necked flask equipped with a stirrer, a thermometer and a dropping funnel was charged with veratrole (2 kg, 14.47 mol) and glacial acetic acid (6 L). Nitric acid (70%, 2.81 kg) was added over a period of three hours while the temperature was maintained below 40° (ice-water bath). This was followed by the dropwise addition of nitric acid (90%, 8.76 L) over a two hour period while maintaining the temperature below 30°. The mixture was stirred an additional two hours and poured into a mixture of water (30 L) and ice (2.3 kg). The drowned mixture was filtered. The solid was slurried in water three times (36 L each) and filtered each time. The final filter cake was washed on the funnel with water (10 L ×3) until the pH of the wash water was 6. The damp cake was recrystallized from ethanol (46 L) to yield product 1; 2.91 kg first crop, mp 128°–131° and 100 g second crop, mp 128°–130°. The total yield was 3.01 kg (91%). (Literature, H. Fellner and G. Fellner, Helv. Chim. Acta, 49, 913 (1966), mp 130°–132°; L. Weinberger and A. R. Day, J. Org. Chem., 24, 1451 (1959), mp 125°–132°).

4,5-Dimethoxy-2-nitroaniline(II)

A one gallon steel autoclave was charged with 4,5-dinitroveratrole (477 g, 2.09 mol) and methanolic ammonia, (340±20 g of ammonia gas in 2.5 L of methanol) and the stirred mixture was heated at 110±5° for 5 hours. After cooling to room temperature, the reaction mixture was filtered and the solid product was washed with methanol (100 mL). The product was dried, 25° /1 mmHg, and amounted to 314 g (76%), mp 171°–173°. Literature M. Tomita, S. Uyeo, H. Inoue, O. Watanabe, H. Makino, Y. Mori, T. Kuwabara, and T. Kitsutaka, J. Pharm. Soc. Japan 71, 850 (1951); mp 168°; R. C. Elderfield, H. E. Mertel, T. M. Mitch, I. M. Wempen and E. Werbel, J. Am. Chem. Soc. 77 4816 (1955), mp 167°–169°).

5,6-Dimethoxy-4-methyl-8-nitroquinoline (III)

A mixture of 4,5-dimethoxy-2-nitroaniline (3.96 g, 0.02 mol), arsenic acid (5.68 g, 0.04 mol) and 85% phosphoric acid (20 mL) was placed in a three-neck flask fitted with a thermometer and a dropping funnel. The reaction mixture was warmed to 100° (internal) with stirring and methyl vinyl ketone (2.1 g, 0.03 mol) was added at such a rate that the temperature was maintained at 100°±2°. After all the ketone was added, the mixture was stirred at 100° for an additional 30 min. The dark solution was poured into ice water (100 mL), treated with charcoal (Norit) and filtered. The filtrate was made alkaline (NH4OH) and extracted with chloroform. The extract was washed with water, dried (K2CO3), the solvent was evaporated and the dark residue was refluxed with benzene (100 mL). Insoluble tar was removed by filtration. The orange filtrate was concentrated to ca. 10 mL, placed on a silica gel column and eluted with benzene (ca. 2 L). The solvent was evaporated and the residue was recrystallized (×2) from methanol to give 1.3 g (30%) of the title compound, mp 123°–125°.

Anal. Calcd for $C_{12}H_{12}N_2O_4$ (percent): C, 58.06; H, 4.80; N, 11.28. Found: C, 57.90; H, 4.60; N, 11.37.

4-Methyl-5-hydroxy-6-methoxy-8-nitroquinoline (IV)

4-Methyl-5,6-dimethoxy-8-nitroquinoline (6.21 g, 25 mmol) was dissolved in ethanol (100 mL) containing concentrated hydrochloric acid (4.7 mL). The mixture was heated under reflux for 21 hours, then cooled to 10° and filtered. The solid was washed with cold (10°) ethanol (18 mL) followed by petroleum ether (15 mL) and air-dried to yield 5.41 g (92%) of the title compound, mp 253°–257° (dec).

Anal. Calcd for $C_{11}H_{10}N_2O_4$ (percent): C, 56.41; H, 4.30; N, 11.96. Found: C, 56.41; H, 4.20; N, 12.10.

4-Methyl-5-chloro-6-methoxy-8-nitroquinoline (V)

A solution of the 5-hydroxyquinoline IV (5.25 g, 0.022 mol) in phosphorus oxychloride (75 mL) was heated at 80° for 2 hours. The reaction mixture was poured onto ice and basified with excess ammonium hydroxide. The tan solid was filtered to give 5.8 g of crude product. This material was purified via column chromatography over silica gel and elution with chloroform. The fast-moving yellow band was collected and concentrated to give 3.9 g (69%) of the title compound, mp 167°–169°. Crystallization from ethanol did not raise the melting point. The crude material can also be purified by sublimation.

Anal. Calcd for $C_{11}H_9ClN_2O_3$ (percent): C, 52.29; H, 3.59; Cl, 14.03; N, 11.09. Found: C, 52.04; H, 3.59; Cl, 14.19; N, 11.09.

4-Methyl-5-(3-trifluoromethylphenoxy)-6-methoxy-8-nitroquinoline (VI)

To a solution of 3-trifluoromethylphenol (4.1 g) in 2-ethoxyethanol (45 mL) containing potassium hydroxide (1.37 g) was added the above 5-chloroquinoline VI (5.7 g, 0.023 mol). The mixture was heated at reflux for 8 hr and allowed to cool overnight. The solid was filtered and washed well with cold ethanol to give 5.9 g (69%) of the title compound, mp 206°–208°. An analytical sample was prepared by crystallization from 2-ethoxyethanol, mp 208°–210°.

Anal. Calcd for $C_{18}H_{13}F_3N_2O_4$ (percent): C, 57.15; H, 3.46; F, 15.07; N, 7.40. Found: C, 56.88; H, 3.52; F, 14.77; N, 7.46.

An alternative route to the common intermediate 4-methyl-5-fluoro-6-methoxy-8-nitroquinoline (VI) was shown in Chart No. 2. The experimental details for the preparation of intermediate IX, X, XI, XII, XIII and XIV, together with the conversion of XIV to VI, are presented below.

2-Fluoro-4-nitroanisole (IX)

To a cold (−2°), stirred solution of 285 g. (2.26 mol) of 2-fluoroanisole in 1.1 L of acetic anhydride was added, dropwise, 114 mL of fuming nitric acid (sp. gr. 1.59) at such a rate that the reaction temperature remained between −2° and 0°. The reaction mixture was stirred for 5 hours at this temperature then poured into 4.0 L of water. The suspension was stirred for 1.5 hours, stored for 15 hours, then extracted with methylene chloride (2×1.0 L). The combined extracts were washed with water (2×500 mL), dried over anhydrous magnesium sulfate, then concentrated in vacuo (475 g.). Crystallization from ethanol gave 147.4 g. (38%) of material suitable for further transformation. Additional material (34.5 g.) was obtained from three scouting runs.

Analytically pure product (5.2 g.; 63.4% recovery) was obtained by recrystallizing 8.2 g of the material from 200 mL of ethanol; mp, 105°–106° (Literature, R. C. Elderfield et al., J. Am. Chem. Soc., 68, 1584 (1946)).

Anal. Calcd for $C_7H_6FNO_3$ (percent): C, 49.13; H, 3.53; F, 11.10; N, 8.19. Found: C, 49.07; H, 3.52; F, 11.02; N, 8.19.

4-Amino-2-fluoroanisole (X)

To a cold (5°), stirred solution of 776 g. (3.44 mol) of stannous chloride dihydrate in 1500 mL of concentrated hydrochloric acid was added, dropwise, a solution of 147 g. (0.861 mol) of 2-fluoro-4-nitroanisole in 3.0 L of ethanol at such a rate that the temperature of the reaction mixture did not exceed 23°. The suspension was stirred for 6 hours at room temperature. The ethanol was removed in vacuo at temperatures below 45°, and the residue was diluted with 3.0 L of water then basified with 1.0 L of 50% sodium hydroxide. The temperature of the mixture was maintained below 23° during the dropwise addition of the base.

The suspension was stirred for 30 minutes then extracted with methylene chloride (1×1.5 L; 2×1.0 L). The combined extracts were washed with water (2×1.0 L), dried over anhydrous magnesium sulfate, then concentrated in vacuo; yield, 110.1 g. (90.2%). The material was suitable for further transformation. Additional product (20.3 g) was obtained from two scouting runs.

Analytically pure product (6.5 g.; 74.7% recovery) was obtained by recrystallizing 8.7 g. of the crude product from 50 mL of ethanol; mp, 82°–84° (Literature, mp 82.6°, G. Shiemann and T. Miau, Ber., 1179 (1933)).

Anal. Calcd for $C_7H_8FNO$ (percent): C, 59.57; H, 5.71; F, 13.46; N, 9.92; Found: C, 59.64; H, 5.54; F, 13.46; N, 9.85.

4-Acetamido-2-fluoroanisole (XI)

To a stirred mixture of 8.4 g. (0.06 moL) of 4-amino-2-fluoroanisole (2) and 50 mL of glacial acetic acid was added 10.9 g. (0.107 mol) of acetic anhydride. The reaction mixture was stirred at room temperature for 3 hours then concentrated in vacuo to a solid. The material was crystallized from benzene (300 mL) to yield 10.4 g. (95.4%) of product suitable for further transformation.

Analytically pure material (2.5 g.; 83.3% recovery) was obtained by recrystallizing 3.0 g. of the purified product from 700 mL of cyclohexane; mp, 112°–114° (Literature; mp 112°–112.5°, R. C. Elderfield et al., J. Am. Chem. Soc., 68, 1584 (1946)).

Anal. Calcd. for $C_9H_{10}FNO_2$ (percent): C, 59.01; H, 5.50; F, 10.37; N, 7.65. Found: C, 59.23; H, 5.50; F, 10.43; N, 7.50.

4-Acetamido-2-fluoro-5-nitroanisole (XII)

To a cold (15°), stirred solution of 12.8 g (0.0699 mol) of 4-acetamido-2-fluoroanisole in 55 mL of acetic acid and 27 mL of acetic anhydride was added, dropwise, 6.5 g (0.072 mol) of 70% nitric acid (sp. gr. 1.424) at such a rate that the temperature of the reaction mixture did not exceed 16°. The solution was stirred for 1.5 hours at room temperature then poured into 400 mL of ice-water. The aqueous suspension was extracted with methylene chloride (1×300 mL; 1×200 mL), then the combined extracts were concentrated in vacuo to a solid (13 g). The material was chromatographed on a column of silica gel (300 g) using benzene as the eluent. The fractions containing the required product were combined then concentrated in vacuo. The solid residue was dissolved in methylene chloride (400 mL) and the solution was washed with water, dried over anhydrous magnesium sulfate, then concentrated in vacuo; yield, 10.0 g (62.9%). The material was suitable for further transformation. Additional material (169 g; 44.6%) was obtained from 110 g (0.779 mol) of 4-amino-2-fluoroanisole without isolating the intermediate 4-acetamido-2-fluoroanisole (3).

Analytically pure material was obtained by recrystallizing 10.0 g of the product from 100 mL of benzene; yield, 5.9 g (59% recovery); mp, 165°–166° (Literature, mp 163°–164°, R. C. Elderfield et al., J. Am. Chem. Soc., 68, 1584 (1946)).

Anal. Calcd for $C_9H_9FN_2O_4$ (percent): C, 47.37; H, 3.98; F, 8.33; N, 12.28. Found: C, 47.25; H, 3.90; F, 8.45; N, 12.23.

4-Amino-2-fluoro-5-nitroanisole (XIII)

A mixture of 128 g (0.565 mol) of 4-acetamido-2-fluoro-5-nitroanisole (4) and 645 mL of 20% ethanolic hydrochloric acid was stirred at reflux for 0.5 hour, then the resulting solution was concentrated in vacuo. The residue was suspended in 730 mL of 3% sodium hydroxide, and the suspension was stirred for 1.5 hours at room temperature. The solid was collected on a filter, washed with water (2.0 L), then dried in vacuo; yield, 102 g. (96.9%). The material was suitable for further transformation. Additional material (36.1 g.) was obtained from three scouting runs.

Analytically pure product (10 g.; 62.1% recovery) was obtained by recrystallizing 16.1 g. of the solid from 325 mL of ethanol; m.p. 145°–147° (literature, mp, 142.5°–143.5°, R. C. Elderfield et al., J. Am. Chem. Soc., 68, 1584 (1946)).

Anal. Calcd for $C_7H_7FN_2O_3$ (percent): C, 45.17; H, 3.79; F, 10.21; N, 15.05. Found: C, 45.26; H, 3.76; F, 10.33; N, 15.16.

4-Methyl-5-fluoro-6-methoxy-8-nitroquinoline (XIV)

To a hot (92°), stirred mixture of 54.4 g (0.292 mol) of 4-amino-2-fluoro-5-nitroanisole (XIII), 50.2 g (0.218 mol) of arsenic pentoxide, and 300 mL of 88% phosphoric acid was added 24.5 g (0.349 mol) of methyl vinyl ketone, during 0.5 hour. The reaction mixture was heated at 95° for 2.5 hours, cooled, diluted with 2.0 L of ice-water, then basified with 700 mL of concentrated ammonium hydroxide. The solid which separated was collected on a filter, washed with water (4×1.0 L), then air dried; yield, 140.6 g. The material was extracted with chloroform (2.0 L). The extract was concentrated to 500 mL then chromatographed on a column of silica gel (900 g) using chloroform as the eluent. The fractions containing product were combined then concentrated in vacuo to a solid; yield, 21.8 g (31.6%). The product was suitable for further transformation. Additional material (40.2 g) was obtained from a similar run and a scouting run.

Analytically pure material (7.6 g; 73.1% recovery) was obtained by recrystallizing 10.4 g of crude product from 75 mL of ethyl acetate; mp, 142°–144°.

Anal. Calcd for $C_{11}H_9FN_2O_3$ (percent): C, 55.94; H, 3.84; F, 8.04; N, 11.86. Found: C, 56.04; H, 3.83; F, 8.30; N, 11.98.

4-Methyl-6-methoxy-8-nitro-5-(3-trifluoromethylphenoxy) quinoline (VI)

From Compound XIV, Alternative Route (Chart No. 2)

4-Methyl-5-fluoro-6-methoxy-8-nitroquinoline (XIV) (24 mg, 0.10 mmol), m-hydroxybenzotrifluoride (18 mg, 0.11 mmol) and potassium carbonate (76 mg) were placed in a small flask. Acetone (1 mL) was added and the mixture was heated at 60° for 4 hours. Gas liquid chromatography indicated complete reaction. The mixture was filtered and the filtrate was extracted with chloroform (×5). The combined extract was washed with 5% aq. potassium carbonate and dried ($MgSO_4$). The solvent was removed (aspirator). The residue was pumped under high vacuum (0.1 mmHg) for 3 hours to yield 38 mg (97%) of yellow crystals of the title compound, mp 214°-215°, mixture mp with an authentic sample, 213°-215°. The retention time of product by gas liquid chromatography was identical also with the authentic sample.

4-Methyl-5-(3-trifluoromethylphenoxy)-6-methoxy-8-aminoquinoline (VII)

A solution of 4-methyl-5-(3-trifluoromethylphenoxy)-6-methoxy-8-nitroquinoline (VI, 5.9 g, 15.6 mmol) in ethanol-dioxane (4:3, v/v, 350 mL) containing wet Raney nickel (ca. 4 g) was reduced at 45 psig for 1¼ hour. The catalyst was filtered and the filtrate was concentrated to dryness. The residual solid was crystallized from ligroin (bp 60°-80°) to afford 4.1 g (76%) of the title compound mp 113°-115°. A sample recrystallized once again gave an analytical sample, mp 116°-117°.

Anal. Calcd for $C_{18}H_{15}F_3N_2O_2$ (percent): C, 62.07; H, 4.34; F, 16.36; N, 8.04. Found: C, 62.24; H, 4.16; F, 16.56; N, 8.08.

4-Methyl-5-(3-trifluoromethylphenoxy)-6-methoxy-8-(4-phthalimido-1-methylbutylamino)quinoline (VIII)

A mixture of the above-8-aminoquinoline (VII 3.0 g, 8.6 mmol), 4-iodo-1-phthalimidopentane (IPP) 3.0 g, 8.7 mmol), triethylamine (TEA) (1.2 mL) and 2-ethoxyethanol (6 mL) was heated at 105° for 2.5 hours, after which time an additional quantity of IPP (3 g) and TEA (1.2 mL) was added. After an additional 4 hours at 105°, the mixture was cooled and dissolved in chloroform. The chloroform solution was washed with 10% aqueous potassium hydroxide and with water, dried and concentrated to dryness. The residue was dissolved in ether and excess ethereal HCL was added. The ether was decanted and the gum was triturated in fresh ether (×2). The gum was then shaken with ether and 10% aqueous potassium carbonate. The ether was removed and the residue was heated in ethanol (15 mL). The mixture was cooled and the solid was filtered to give 1.65 g of the title compound. The filtrate was concentrated to dryness and the residue was triturated in hot ligroin (bp 60°-80°, 50 mL). The ligroin was decanted from a little insoluble gum and concentrated to dryness to afford 1.5 g of additional crude product. The combined crops were crystallized from ethanol (75 mL) to give 2.75 g (57%) of pure title compound, mp 143°-145°.

Anal. Calcd for $C_{31}H_{28}F_3N_3O_4$ (percent): C, 66.07; H, 5.01; F, 10.11; N, 7.46. Found: C, 65.78; H, 5.10; F, 9.94; N, 7.62.

8-(4-Amino-1-methylbutylamino)-6-methoxy-4-methyl-5-(3-trifluoromethylphenoxy)quinoline Succinate (1)

A solution of the phthalimide VIII (4.9 g, 8.7 mmol) in ethanol (110 mL) containing hydrazine hydrate (75%, 1.48 mL) was heated at reflux for 6 hours. The ethanol was removed under reduced pressure and the residue was shaken with ether and 10% aqueous potassium hydroxide. The ether layer was washed with water (×2) and dried ($K_2CO_3$). To the dried ether solution of 1 as the free base, was added a solution of succinic acid (1.03 g, 1 mol equiv) in ether (100 mL) containing methanol (4 mL) to solubilize the succinic acid. After standing overnight, the solid was filtered to yield 4.5 g (94%) of the target compound (1), mp 102°-103° (eff).

Anal. Calcd for $C_{23}H_{26}F_3N_3O_2 \cdot C_4H_6O_4$ (percent): C, 58.79; H, 5.85; F, 10.33; N, 7.62. Found: C, 58.52; H, 5.69; F, 10.17; N, 7.42.

EXAMPLE 2

8-((4-Amino-1-pentyl)amino)-6-methoxy-4-methyl-5-(3-trifluoromethylphenoxy)-quinoline Hemisuccinate(2)

A solution of 8-amino-6-methoxy-4-methyl-8-(3-trifluoromethylphenoxy)quinoline (5.26 g, 15 mmol), 1-iodo-4-phthalimidopentane (5.26 g, 15 mol) in 2-ethoxyethanol (25 mL) was heated at 110° for 1.5 hour after which time an additional 7.5 mmol of iodophthalimidopentane and triethylamine were added. After stirring 1.5 hour an additional 7.5 mmol of each reagent was added. After stirring an additional 4.5 hours the reaction mixture was diluted with $CH_2Cl_2$ and the organic layer was washed with water (×3). After drying ($K_2CO_3$) the organic layer was concentrated to dryness and the residue was chromatographed over a silica gel column (33 mm×500 mm). Elution with chloroform afforded the intermediate phthalimide (6.65 g, 79%) which could be crystallized from EtOH to give mp 122°-124°.

Anal. Calcd for $C_{31}H_{28}F_3N_3O_4$ (percent): C, 66.07; H, 5.01; N, 7.46; Found: C, 66.37; H, 4.97; N, 7.46.

The above phthalimide (7.5 g, 14.8 mmol) was heated at reflux with hydrazine hydrate (75%, 2.2 mL) in EtOH (125 mL) for 9 hours as described in Example 1. The crude oily free base was dissolved in MeOH and a solution of succinic acid (0.88 g, 7.4 mmol) in MeOH (10 mL) was added. The solution was concentrated to dryness and the solid residue was crystallized from acetonitrile (100 mL) to yield the succinate salt (5.2 g), mp 165°-9°. Recrystallization from EtOH gave 3.9 g (53%), mp 177°-178.5° of the title compound.

Anal. Calcd for $C_{23}H_{26}F_3N_3O_2 \cdot \frac{1}{2} C_4H_6O_4$ (percent): C, 60.97; H, 5.93; F, 11.57; N, 8.53. Found: C, 61.07; H, 5.95; F, 11.47; N, 8.60.

EXAMPLE 3

8-((5-Amino-1-hexyl)amino)-6-methoxy-4-methyl-5-(3-trifluoromethylphenoxy)quinoline Hemisuccinate Hydrate (3)

The title compound was prepared via the procedure described above in Example 2. The yield of the phthalimide intermediate was 57%, mp 109.5°-111° (eff., EtOH).

Anal. Calcd. for $C_{32}H_{30}F_3N_3O_4$ (577.6) C, 66.54; H, 5.24; N, 7.27. Found: C, 66.38; H, 5.04; N, 7.33.

The phthalimide intermediate (10 g, 17.3 mmol) was converted to the target diamine 3 as described in Example 1. The yield was 75%, mp 149°-151° (EtOH, dried in vacuo at 78°).

Anal. Calcd for $C_{24}H_{28}F_3N_3O_2 \cdot 0.5\ C_4H_6O_4 \cdot H_2O$ (percent): C, 59.53; H, 6.34; F, 10.87; N, 8.01. Found: C, 59.27; H, 6.37; F, 11.00; N, 8.08.

EXAMPLE 4

8-((4-Amino-1-ethylbutyl)amino)-6-methoxy-4-methyl-5-(3-trifluoromethylphenoxy)-quinoline Succinate (4)

A solution of 8-amino-6-methoxy-4-methyl-5-(3-trifluoromethylphenoxy)-quinoline (10 g, 29 mmol), prepared as in Example 1, 4-iodo-1-phthalimidohexane (IPH, 10 g, 28 mmol), triethylamine (TEA, 4.5 mL) and 2-ethoxyethanol (10 mL) were heated at 115° for 2½ hours. One equivalent of IPA and TEA was added and the solution was heated at 115° an additional 2.5 hours. Then one-half equivalent each of IPH and TEA was added and the reaction mixture was heated 5 hours longer. The reaction mixture was diluted with chloroform and washed with water (×3). The organic layer was dried ($K_2CO_3$) and concentrated to dryness in vacuo. The oily residue was combined with that obtained from another 8.5 g run and chromatographed over a silica gel column (EM Labs.). Elution with $CHCl_3$ and collection of the fast-moving yellow band afforded the desired phthalimide intermediate (ca. 12 g) contaminated with some IPH. The slower moving material, ca. a 1/1 mixture of product and starting 8-aminoquinoline, was then collected and recycled with IPH and TEA as described above. An additional 7 g of crude product was obtained. The crude material from both runs was combined, dissolved in hot isopropyl alcohol and acidified with 2.7 N HCl-i-PrOH. Pure phthalimide hydrochloride was obtained, 13.2 g (40%), mp 185°–7°.

The above material was converted in $CH_2Cl_2$ to the free base with dilute aqueous $NH_4OH$. After drying and concentrating the organic layer, the residue oil was heated in EtOH (125 mL) containing 75% hydrazine hydrate (4.0 mL). Additional hydrazine hydrate was added after 3 hours (2 mL) and after 4½ hours (1 mL). The reaction was heated an additional 2 hours and the reaction mixture was concentrated in vacuo. The residue was shaken with 20% aq KOH and ether and the ether was removed in vacuo. The base (7.5 g) was dissolved in ether (100 mL) and the solution was added to a solution of succinic acid (2.0 g) in ether (325 mL). The slurry was stirred for 3.5 hours and filtered to yield the title compound (8.7 g, 72%), mp 107°–110° (eff), with shrinking at 103°. This material was recrystallized from $CH_3CN$ (140 mL) and filtered after 48 hours to give pure title compound 4, 7.35 g (60%), mp 137°–9° (eff).

Anal. Calcd for $C_{24}H_{28}F_3N_3O_2 \cdot C_4H_6O_4$ (percent); C, 59.46; H, 6.06; F, 10.08; N, 7.43. Found: C, 59.58; H, 5.90; F, 9.80; N, 7.63.

EXAMPLE 5

8-((4-Isopropylamino-1-methylbutyl)amino)-6-methoxy-4-methyl-5-(3-trifluoromethylphenoxy)quinoline Succinate (5)

A solution of 8-(4-amino-1-methylbutylamino)-6-methoxy-4-methyl-5-(3-trifluoromethylphenoxy)quinoline as the free base (4.7 g, 10.8 mmol) prepared as in Example 1 in EtOH (60 mL) containing acetone (1.8 mL), prereduced platinum oxide (0.6 g) and molecular sieves (3A) was reduced on a Parr apparatus at 45 psig for 5 hours. An additional quantity of acetone (0.9 mL) was added and the reduction was continued an additional 18 hours. The catalyst and molecular sieves were filtered (celite) and the solvent was removed in vacuo. The residue was dissolved in acetonitrile (50 mL) and succinic acid (1.35 g, 1 mol equivalent) was added with stirring. The solid was filtered after cooling in the refrigerator overnight to yield the title compound 5, 5.8 g (91%), mp 143°–146°. Recrystallization from acetonitrile (75 mL) yielded pure title compound, 5.2 g, (81%), mp 145°–147.5°.

Anal. Calcd for: $C_{26}H_{32}F_3O_2 \cdot C_4H_6O_4$ (percent): C, 60.70; H, 6.45; F, 7.08; N, 9.60. Found: C, 60.61; H, 6.48; F, 7.23; N, 9.48.

EXAMPLE 6

8-((4-Amino-1-methylbutyl)amino)-6-methoxy-5-(4-methoxyphenoxy)-4-methylquinoline Phosphate (6)

6-Methoxy-5-(4-methoxyphenoxy)-4-methyl-8-nitroquinoline

A solution of 4-methoxyphenol (5.76 g, 46.5 mmol) and KOH (2.61 g, 46.6 mmol) in 2-ethoxyethanol (90 mL) was heated with removal of water until the pot temperature reached 130° after which time 4-methyl-5-chloro-6-methoxy-8-nitroquinoline, prepared as in Example 1 (9 g, 35.7 mmol), was added. The reaction mixture was heated at reflux (130°) for 2 hours and cooled at 5° for 18 hours. Filtration afforded the title compound (8.25 g, 68%), mp 158°–60°.

Anal. Calcd for: $C_{13}H_{16}N_2O_5$ (percent): C, 63.52; H, 4.74; N, 8.23. Found: C, 63.63; H, 4.77; N, 8.31.

8-Amino-6-methoxy-5-(4-methoxyphenoxy)-4-methylquinoline

A solution of the above-8-nitroquinoline (13.7 g, 40.3 mmol), and 1/1 dioxane-ethanol (1L) containing wet Raney nickel (ca. 10 g) was reduced at 45 psig for one hour. The catalyst was filtered (celite) and the filtrate was concentrated to dryness in vacuo. The residue was crystallized from toluene (100 mL) to afford the title compound (7.2 g, 58%), mp 185°–187°.

Anal. Calcd for: $C_{18}H_{18}N_2O_3$ (percent): C, 69.86; H, 5.85; N, 9.03. Found: C, 69.98; H, 5.77; N, 9.28.

6-Methoxy-5-(4-methoxyphenoxy)-4-methyl-8-((4-phthalimido-1-methylbutyl)amino)quinoline Hydrochloride A solution of the above 8-aminoquinoline (7.1 g, 22.9 mmol), 4-iodo-1-phthalimidopentane (7.9 g, 22.9 mmol), triethylamine (3.3 mL, 23 mmol, in 2-ethoxyethanol (40 mL) was heated at 110°–115° for 1½ hours. An additional equivalent of IPP and $Et_3N$ were added and heating was continued 2 hours longer. An additional 0.5 equivalent of IPP and $Et_3N$ were added and the mixture was heated an additional 2 hours. The reaction mixture was diluted with $CHCl_3$ and washed with water (×2). The organic layer was dried ($K_2CO_3$) and concentrated under reduced pressure. The residue was slurried in ether and filtered to remove some dark, insoluble material. Excess ethereal hydrogen chloride was added to the filtrate and the orange solid was filtered. The crude product was crystallized from ethanol (290 mL); to yield the title compound (8.2 g, 71%), mp 189°–191°.

Anal. Calcd for: $C_{31}H_{31}N_3O_5 \cdot HCl$ (percent): C, 66.25; H, 5.74; N, 7.48. Found: C, 66.18; H, 5.75; N, 7.64.

8-((4-Amino-1-methylbutyl)amino)-6-methoxy-5-(4-methoxyphenoxy)-4-methylquinoline Phosphate (6)

The above phthalimide hydrochloride (7.8 g, 15.5 mmol) was converted to the base by shaking with $CH_2Cl_2$ and dilute ammonium hydroxide. The organic layer was dried ($K_2CO_3$) and concentrated in vacuo. The residual base was dissolved in EtOH (300 mL) containing hydrazine hydrate (75%, 2.5 mL) and heated at reflux for 3½ hours. Additional hydrazine hydrate (2.5 mL) was added and the mixture was heated an additional 3 hours. The reaction mixture was concentrated to dryness and the residue was shaken with ether and 20% aqueous KOH. The organic layer was dried ($K_2CO_3$) and concentrated. The target base was dissolved in a mixture EtOH (65 mL) and $H_2O$ (9 mL) and 1 M ethanolic phosphoric acid (13 mL, 13 mmol) was added. The mixture was heated (steam bath) to dissolve the precipitated gum. After cooling at 5° overnight the precipitated solid was collected to yield the title compound 6 which was dried at 70° (0.1 mm Hg). The yield was 6.4 g (84%), mp 162°–163°.

Anal. Calcd for: $C_{23}H_{29}N_3O_3.H_3PO_4$ (percent): C, 55.98; H, 6.54; N, 8.51; P, 6.28. Found: C, 55.78; H, 6.64; N, 8.51; P, 6.47.

EXAMPLE 7

8-((4-Amino-1-methylbutyl)amino)-5-(3,4-dichlorophenoxy)-6-methoxy-4-methylquinoline Phosphate (7)

The title compound was prepared as in Example 6 using 3,4-dichlorophenol instead of 4-methoxyphenol. The phthalimide intermediate (7 g, 12.4 mmol) was converted to the title compound 7 6.1 g (92%), mp 199°–201° (EtOH-H₂O).

Anal. Calcd for: $C_{22}H_{26}Cl_2N_3O_2.H_3PO_4$ (percent); C, 49.54; H, 5.48; N, 7.88; P, 5.81. Found: C, 49.85; H, 5.32; N, 8.06; P, 5.84.

EXAMPLE 8

8-((4-Amino-1-methylbutyl)amino))-5-(2,4-dichlorophenoxy)-6-methoxy-4-methylquinoline Phosphate(8)

5-(2,4-Dichlorophenoxy)-6-methoxy-4-methyl-8-nitroquinoline

The title compound was prepared from 5-chloro-6-methoxy-4-methyl-8-nitroquinoline from Example 1 (15 g, 0.06 mol), 2,4-dichlorophenol (38 g, 0.23 mol), potassium hydroxide (13.2 g, 0.24 mol) and 2-ethoxyethanol (150 mL) as described in Example 1. The yield was 14.5 g (64%), mp 165.5°–168°.

Anal. Calcd for: $C_{17}H_{12}Cl_2N_2O_4$ (percent): C, 53.85; H, 3.19; Cl, 18.70; N, 7.39. Found: C, 53.67; H, 2.98; Cl, 18.50; N, 7.68.

8-Amino-5-(2,4-dichlorophenoxy)-6-methoxy-4-methylquinoline

The title compound was prepared from the above 8-nitroquinoline (13 g, 0.034 mol) and wet Raney nickel (ca. 5 g) in dioxane (325 mL) and ethanol (490 mL) as described earlier for the 5-(4-methoxyphenoxy) analog. The yield was 10 g (84%), mp 115°–117.5° (cyclohexane).

Anal. Calcd for: $C_{17}H_{14}Cl_2N_2O_2$ (percent): C, 58.46; H, 4.04; N, 8.02. Found: C, 58.48; H, 4.13; N, 8.14.

5-(2,4-Dichlorophenoxy)-6-methoxy-4-methyl-8-((4-phthalimido-1-methylbutyl)amino)quinoline The title compound was prepared from the above 2,4-dichlorophenoxyquinoline (9 g, 0.026 mol). The crude oil obtained after concentration of the chloroform layer was crystallized from ether (175 mL) to afford the title compound (8.0 g, 54%), mp 168°–170°. A sample (1.0 g) was recrystallized from 2-ethoxyethanol (10 mL) to give 0.9 g (90%), mp 170°–172°.

Anal. Calcd for: $C_{30}H_{23}Cl_2N_3O_4$ (percent): C, 63.76; H, 4.99; N, 7.43. Found: C, 63.98; H, 5.00; N, 7.62.

8-((4-Amino-1-methylbutyl)amino)-5-(2,4-dichlorophenoxy-6-methoxy-4-methylquinoline Phosphate (8)

The title compound was prepared from the above phthalimido intermediate (7.5 g, 13 mmol) as described in Example 6. The yield was 5.35 g (76%), mp 203°–206° (EtOH-H₂O, 9/1).

Anal. Calcd for: $C_{22}H_{26}Cl_2N_3O_2.H_3PO_4$ (percent): C, 49.54; H, 5.48; N, 7.88; P, 5.81. Found: C, 49.55; H, 5.27; N, 7.82; P, 5.63.

EXAMPLE 9

8-((4-Amino-1-methylbutyl)amino)-5-(4-fluorophenoxy)-6-methoxy-4-methylquinoline Phosphate (9)

5-(4-Fluorophenoxy)-6-methoxy-4-methyl-8-nitroquinoline

In a 1—1, three-necked flask were placed potassium hydroxide (19.3 g, 0.304 mol) 4-fluorophenol (36.8 g, 0.328 mol) and 2-ethoxyethanol (100 mL). The mixture was heated with mechanical stirring until a homogeneous red solution was obtained. 4-Methyl-5-chloro-6-methoxy-8-nitroquinoline (59.2 g, 0.234 mol) was added and the additional funnel was rinsed with 2-ethoxyethanol (300 mL). The mixture was heated to reflux (110°). Distillate (138 mL) was collected until a reflux temperature of 131°–132° was obtained (ca. 30 min). The dark mixture was allowed to cool (ice-bath) for several hours and filtered. The collected solid was washed with cold 2-ethoxyethanol (50 mL) and with cold ethanol (2×40 mL). The filter cake was slurried with cold water (300 mL) and filtered. The solid was washed with cold water (3×50 mL), and air-dried to give crude product (51.2 g).

This material was recrystallized from 2-ethoxyethanol (750 mL) with charcoaling. The hot solution was filtered through a steam-heated funnel and the filtrate was allowed to cool. The product was collected as yellow platelets, 40.5 g (53%), mp 184°–185.5° with softening at 182°. The mother liquor was concentrated to 150 mL to yield a second crop (5.7 g). The second crop was recrystallized from 2-ethoxyethanol (80 mL) with charcoaling to give additional product, 4.8 g (6.0%), mp 183.5°–185°. An analytical sample, mp 183.5°–185°, was obtained by recrystalling a portion of the first crop.

Anal. Calcd for $C_{17}H_{13}FN_2O_4$ (percent): C, 62.22; H, 3.99; F, 5.79; N, 8.53. Found: C, 62.49; H, 4.08; F, 5.72; N, 8.82.

8-Amino-5-(4-fluorophenoxy)-6-methoxy-4-methylquinoline 5-(4-Fluorophenoxy-6-methoxy-8-nitro-4-methylquinoline (20.2 g, 61.5 mmol) was dissolved in hot p-dioxane (500 mL), diluted with hot ethanol (500 mL), and placed in a 2-L Parr bottle with Raney nickel (ca. 10 g). The reaction was hydrogenated at 50 psig for one hr. The catalyst was removed by filtration through celite and the filtrate was concentrated in vacuo affording a brownish-orange oil. The above procedure was repeated and the combined crude oil was recrystallized from cyclohexane (1200 mL) with charcoaling. The product was collected, washed with cold petroleum ether, 2×50 mL and air-dried to give pure title compound 28.8 g (78%), mp 143°–144° with softening at 141°. Recrystallization in the same way gave an analytical sample, mp 144.5°–145.5°, with softening at 142°.

Anal. Calcd for $C_{17}H_{15}FN_2O_2$ (percent): C, 68.45; H, 5.07; F, 6.37; N, 9.39. Found: C, 68.15; H, 5.14; F, 6.58; N, 9.37.

5-(4-Fluorophenoxy)-6-methoxy-4-methyl-8-((4-phthalimido-1-methylbutyl)aminoquinoline A mixture of 4-methyl-8-amino-5-(4-fluorophenoxy)-6-methoxyquinoline (36.0 g, 0.121 mol), 4-iodo-1-phthalimidopentane (41.4 g, 0.121 mol,), triethylamine (12.2 g, 0.120 mol) and 2-ethoxyethanol (75 mL) was stirred and heated in an oil bath at 100°–105° (bath temperature) for 4 hours. After standing overnight at room temperature, additional 4-iodo-1-phthalimidopentane (41.4 g, 0.121 mol) and triethylamine (12.2 g) were added. Heating was continued at 105°–110° (oil bath) for an additional 4 hours (8 hours total). The solution was cooled to room temperature, dissolved in chloroform (200 mL), and washed successively with aq. potassium hydroxide (6.5 g, in 200 mL water), water (2×200 mL), and finally with brine (50 mL). The chloroform solution was dried (potassium carbonate), filtered, and the solvent was removed under aspirator pressure.

The residual oil was dissolved in ether (1.2 L). A solution of anhydrous hydrogen chloride in isopropanol (about 4 M, 36 mL) was added to precipitate the hydrochloride salt. Thorough trituration overnight was necessary to produce a uniform crystalline solid. The hydrochloride salt was collected and washed with ether (100 mL). After air drying there was obtained 61.6 g (39%) of a red-orange solid.

The hydrochloride salt was dissolved in chloroform (0.5 L) and washed successively with 5% aq. potassium carbonate, water and brine. The chloroform solution was dried over anhydrous potassium carbonate, filtered, and the solvent was removed under aspirator pressure. The residue was crystallized twice from ethanol to yield 40.3 g, (61%) of the title compound, mp 123°–126°.

Anal. Calcd for $C_{30}H_{28}FN_3O_4$ (percent): C, 70.16; H, 5.50; F, 3.70; N, 8.18. Found: C, 70.13; H, 5.44; F, 3.83; N, 8.26.

8-((4-Amino-1-methylbutyl)amino)-5-(4-fluorophenoxy)-6-methoxy-4-methylquinoline phosphate (9)

A mixture of 5-(4-fluorophenoxy)-6-methoxy-4-methyl-8-((4-phthalimido-1-methylbutyl)amino)quinoline (39.4 g, 76.7 mmol), hydrazine (75% aq solution, 12.6 mL 0.192 mol) and ethanol (1 L) was heated under reflux for 9 hours. After cooling to room temperature, water (175 mL) was added and most of the ethanol was removed under reduced pressure. Aqueous potassium hydroxide (8.6 g, 0.15 mol), in 100 mL water) and ether (0.5 L) were added and the mixture was shaken in a separatory funnel. The layers were separated; the water layer was extracted further with ether (250 mL, 100 mL); and the combined ether layers were washed successively with water (3×250 mL) and with brine. The solution was dried ($K_2CO_3$), filtered, and evaporated to a thick oil, 31.6 g (107%), under reduced pressure.

The oil was dissolved in ethanol (0.5 L) and treated with alcoholic phosphoric acid (4 mL, 6.8 g, in 100 mL ethanol). A thick gum separated which crystallized upon standing. The yellow solid was collected and washed successively with ethanol (2×50 mL) and with ether (2×50 mL) to give after air drying 33.1 g (90%) of crude product. This material was dissolved in boiling ethanol-methanol (800 mL-200 mL), filtered white hot, and cooled slowly with seeding and stirring. The yellow product was collected washed successively with ethanol (2×50 mL) and with ether to give, after drying at 65°–70°/1 mm Hg for 24 hours, 17.9 g of product. A second crop (10.3 g) was obtained by concentration of the mother liquors. The two crops (28.2 g) were dissolved in hot methanol (100 mL). The solution was diluted with hot ethanol (500 mL), and solvent (150 mL) was removed by distillation. Slow, controlled cooling with seeding and stirring afforded crystalline title compound, 21.4 g (58%), mp above 113° (gradual), after drying at 65°–70°/1 mm Hg for 48 hours.

Anal. Calcd for $C_{22}H_{26}FN_3O_2.H_3PO_4$ (percent): C, 54.88; H, 6.07; F, 3.94; N, 8.73; P, 6.43. Found: C, 54.54; H, 6.18; F, 3.72; N, 8.91; P, 6.35.

We claim:

1. A compound of the formula:

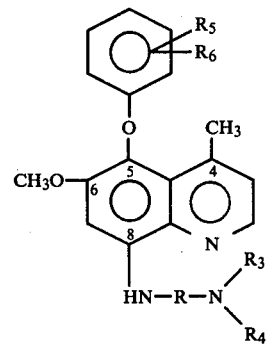

wherein R is an alkylene group which is

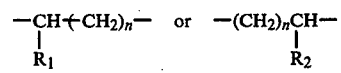

wherein n is 3 or 4, wherein $R_1$ and $R_2$ are methyl or ethyl; wherein $R_3$ is hydrogen and $R_4$ is hydrogen, wherein $R_5$ and $R_6$ are hydrogen, chloro, bromo, fluoro, trifluoromethyl or methoxy groups and wherein the compound is a free amine or a pharmaceutically acceptable acid amine salt.

2. The compound of claim 1 wherein R is

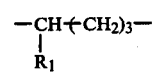

and wherein $R_1$ is methyl.

3. The compound of claim 1 wherein $R_5$ is trifluoromethyl and $R_6$ is hydrogen.

4. The compound of claim 1 wherein $R_5$ and $R_6$ are both chloro groups.

5. The compound of claim 1 wherein $R_5$ and $R_6$ are meta and para or ortho and para dichloro groups.

6. The compound of claim 1 as the succinate or phosphate acid amine salt.

7. The compound of claim 1 wherein $R_5$ is methoxy and $R_6$ is hydrogen.

8. The compound of claim 1 wherein $R_5$ is fluoro and $R_6$ is hydrogen.

9. The compound of claim 1 which is 8-((4-amino-1-methylbutyl)amino)-6-methoxy-4-methyl-5-(3-trifluoromethylphenoxy)quinoline as a free amine or a pharmaceutically acceptable acid amine salt.

10. The compound of claim 1 which is 8-((4-amino-1-methylbutyl)amino)-5-(4-fluorophenoxy)-6-methoxy-4-methylquinoline as a free amine or as a pharmaceutically acceptable acid amine salt.

11. The compound of claim 1 which is 8-((4-amino-1-methylbutyl)amino)-6-methoxy-5-(4-methoxyphenoxy)-4-methylquinoline as a free amine or as a pharmaceutically acceptable acid amine salt.

12. The compound of claim 1 which is 8-((4-amino-1-methylbutyl)amino)-5-(3,4-dichlorophenoxy)-6- methoxy-4-methylquinoline as a free amine or a pharmaceutically acceptable acid amine salt.

13. The compound of claim 1 which is 8-((4-amino-1-methylbutyl)amino)-5-(2,4-dichlorophenoxy)-6-methoxy-4-methylquinoline as a free amine or as a pharmaceutically acceptable acid amine salt.

14. The compound of claim 1 which is 8-((4-amino-1-ethylbutyl)amino-6-methoxy-4-methyl-5-(3-trifluoromethylphenoxy)quinoline as a free amine or as a pharmaceutically acceptable acid amine salt.

* * * * *